United States Patent
Elbashir et al.

(10) Patent No.: US 12,091,318 B2
(45) Date of Patent: Sep. 17, 2024

(54) PROCESSING METHANE FOR SYNGAS PRODUCTION WITH REDUCED $CO_2$ EMISSIONS

(71) Applicant: Qatar Foundation for Education, Science and Community Development, Doha (QA)

(72) Inventors: Nimir Elbashir, Doha (QA); Shaik Afzal, Doha (QA); Mahmoud El-Halwagi, Doha (QA); Debalina Sengupta, Doha (QA)

(73) Assignee: QATAR FOUNDATION FOR EDUCATION, SCIENCE AND COMMUNITY DEVELOPMENT, Doha (QA)

( * ) Notice: Subject to any disclaimer, the term of this patent is extended or adjusted under 35 U.S.C. 154(b) by 775 days.

(21) Appl. No.: 17/040,802

(22) PCT Filed: Apr. 3, 2019

(86) PCT No.: PCT/QA2019/050008
§ 371 (c)(1),
(2) Date: Sep. 23, 2020

(87) PCT Pub. No.: WO2019/194694
PCT Pub. Date: Oct. 10, 2019

(65) Prior Publication Data
US 2021/0009411 A1     Jan. 14, 2021

Related U.S. Application Data

(60) Provisional application No. 62/652,110, filed on Apr. 3, 2018.

(51) Int. Cl.
*C01B 3/34* (2006.01)
*C01B 32/40* (2017.01)
(Continued)

(52) U.S. Cl.
CPC ............... *C01B 3/34* (2013.01); *C01B 32/40* (2017.08); *C07C 1/04* (2013.01);
(Continued)

(58) Field of Classification Search
CPC ... C01B 3/34; C01B 32/40; C01B 2203/0238; C01B 2203/0415; C01B 2203/047;
(Continued)

(56) References Cited

U.S. PATENT DOCUMENTS 3,317,275 A * 5/1967 Tate ..................... B01D 53/62
423/418
5,073,356 A 12/1991 Guro et al.
(Continued)

FOREIGN PATENT DOCUMENTS

WO     2019194694 A2    10/2019

OTHER PUBLICATIONS

Cao et al., Synthesis Gas Production with an Adjustable H2/CO Ratio through the Coal Gasification Process: Effects of Coal Ranks And Methane Addition, 2008, Energy & Fuel, 22, 1720-1730 (Year: 2008).*
International Search Report for related International Application No. PCT/QA2019/050008; report dated Sep. 1, 2020; (2 pages).
Written Opinion for related International Application No. PCT/QA2019/050008; report dated Sep. 1, 2020; (5 pages).

*Primary Examiner* — Stefanie J Cohen
*Assistant Examiner* — Ritu S Shirali
(74) *Attorney, Agent, or Firm* — K&L Gates LLP (57) ABSTRACT

A method for processing methane includes processing methane in presence of a carbon dioxide stream, whereby a synthesis gas including carbon monoxide and hydrogen is produced. The synthesis gas is contacted with a carbon monoxide-absorbing solution, thereby removing at least a portion of the carbon monoxide and producing a final synthesis gas having an increased ratio of hydrogen to carbon monoxide.

6 Claims, 10 Drawing Sheets

(51) Int. Cl.
*C07C 1/04* (2006.01)
*C07C 9/04* (2006.01)

(52) U.S. Cl.
CPC ........... *C01B 2203/0238* (2013.01); *C01B 2203/0415* (2013.01); *C01B 2203/047* (2013.01); *C01B 2203/1241* (2013.01); *C07C 9/04* (2013.01)

(58) Field of Classification Search
CPC ..... C01B 2203/1241; C01B 3/38; C07C 1/04; C07C 9/04; Y02P 20/582
USPC ......................................................... 252/373
See application file for complete search history.

(56) References Cited

U.S. PATENT DOCUMENTS

| | | | |
|---|---|---|---|
| 2002/0085963 A1* | 7/2002 | Vidalin | C07C 29/152 422/187 |
| 2003/0236312 A1 | 12/2003 | O'Rear | |
| 2008/0319093 A1 | 12/2008 | Olah et al. | |
| 2011/0132193 A1 | 6/2011 | Lechnick et al. | |
| 2014/0264176 A1* | 9/2014 | Wynn | B01D 53/226 252/373 |
| 2017/0204335 A1 | 7/2017 | Ravikumar | |

\* cited by examiner

PROCESSING METHANE FOR SYNGAS PRODUCTION WITH REDUCED CO₂ EMISSIONS

CROSS-REFERENCE TO RELATED APPLICATIONS

The present application is a National Stage of International Application No. PCT/QA2019/050008, filed on Apr. 3, 2019, which claims the benefit of U.S. Provisional Patent Application No. 62/652,110, filed Apr. 3, 2018, the disclosure of which is incorporated into this specification by reference in its entirety.

BACKGROUND

The US Environmental Protection Agency (EPA) and the Intergovernmental Panel on Climate Change (IPCC), both estimate that CO₂ constitutes more than 76% of all anthropogenic emissions. One of the strategies proposed to reduce greenhouse gas emissions is Carbon Capture, and Utilization (CCU). CCU processes involve the capture of CO₂ and reuse as reactants. One of the popular CCU processes is Dry Reforming of Methane (DRM). The reaction proceeds as follows:

$$CH_4 + CO_2 \rightarrow 2H_2 + 2CO \quad \Delta H_{298} = 247 \text{ kJ/mol} \quad (1)$$

In contrast, the current commercial processes to produce syngas are Steam Methane Reforming (SMR) and Partial Oxidation of Methane (POx) which utilize steam and oxygen as shown in the reactions:

$$\text{SMR } CH_4 + H_2O \rightarrow CO + 3H_2 \quad 206 \text{ kJ/mol} \quad (2)$$

$$\text{POx } CH_4 + \tfrac{1}{2}O_2 \rightarrow CO + 2H_2 \quad -36 \text{ kJ/mol} \quad (3)$$

Unlike SMR and POx, DRM has CO₂ as a reactant which earns it a credit while computing the carbon balance of the process. The high CO₂ content in natural gas feeds has also generated interest in the DRM process. There are three main challenges for the commercialization of a DRM process. Firstly, the energy requirement of DRM process is higher at 247 kJ/mol when compared to that of an SMR (206 kJ/mol), which is currently the major technology to produce hydrogen and hydrogen-rich syngas in the industry. Secondly, the low H₂/CO ratio (syngas ratio) of DRM syngas hinders its commercial application for many downstream processes which require higher syngas ratios. And lastly, the absence of steam and oxygen accelerates catalyst deactivation by coking pathways. Accordingly, it is desirable to provide an improved DRM process.

SUMMARY

The present disclosure provides processes involving post DRM treatment of syngas without the use of steam or oxygen as oxidants, to produce high-quality syngas. This will help to reduce the overall carbon footprint of syngas production processes. In brief, they involve removal of CO from DRM syngas (using COSORB Process or any other embodiment as described) and the addition of H₂ from an external source to DRM syngas. Economic and environmental metrics have been used to compare these processes with current benchmark technologies to show the potential of these processes. All major sources of emissions in each process pathway have been quantified and the performance of each case is measured in terms of overall CO₂ emissions and operating costs. An optimization-based approach was used to find operating points which maximize syngas production, and also have the lowest carbon footprint for that specific syngas production.

According to one non-limiting aspect of the present disclosure, an example embodiment of a method for processing methane is described. The example method for processing methane includes processing methane in presence of a carbon dioxide stream, whereby a synthesis gas including carbon monoxide and hydrogen is produced. The synthesis gas is contacted with a carbon monoxide-absorbing solution, thereby removing at least a portion of the carbon monoxide and producing a final synthesis gas having an increased ratio of hydrogen to carbon monoxide. In one embodiment, the removed carbon monoxide is used as feedstock for an external plant.

According to another non-limiting aspect of the present disclosure, an example embodiment of a method for processing methane includes processing methane in presence of a carbon dioxide stream, whereby a synthesis gas including carbon monoxide and hydrogen is produced. The synthesis gas is blended with hydrogen provided from an ethylene plant, thereby producing a final synthesis gas having an increased ratio of hydrogen to carbon monoxide According to another non-limiting aspect of the present disclosure, an example embodiment of a method for processing methane includes processing methane in presence of a carbon dioxide stream, whereby a synthesis gas including carbon monoxide and hydrogen is produced. The synthesis gas is blended with hydrogen provided from an external source, thereby producing a final synthesis gas having an increased ratio of hydrogen to carbon monoxide.

Additional features and advantages are described herein, and will be apparent from the following Detailed Description and the figures.

BRIEF DESCRIPTION OF THE DRAWINGS

Features and advantages of the processes described herein may be better understood by reference to the accompanying drawings in which.

The reader will appreciate the foregoing details, as well as others, upon considering the following detailed description of certain non-limiting embodiments of the processes according to the present disclosure. The reader may also comprehend certain of such additional details upon using the processes described herein.

DETAILED DESCRIPTION

The present disclosure, in part, is generally related to reducing $CO_2$ emissions of reforming processes with different reformer networks incorporating a DRM unit. As described herein, in some embodiments a method for dry reforming of methane includes removal of CO from DRM syngas and addition of $H_2$ from an external source. The present inventors have surprisingly discovered that the removal of CO from DRM syngas can result in a reduction of overall $CO_2$ emissions for syngas production of comparable syngas ratios and also a reduction of operating costs in the conditions specified. Addition of $H_2$ from an external source to the DRM syngas stream also has a small benefit in reducing $CO_2$ emissions and operating cost, as described herein.

According to certain non-limiting embodiments, the removed carbon monoxide is used either as fuel or exported to an external customer. Depending on the usage requirements or preferences for the particular customer, the latter option may be more attractive economically and environmentally.

In certain non-limiting embodiments, the ratio of hydrogen to carbon monoxide in the final synthesis gas is at least 1.5, at least 1.6, at least 1.7, at least 1.8, at least 1.9, at least 2.0, at least 2.1, at least 2.2, at least 2.3, at least 2.4, at least 2.5, at least 2.6, at least 2.7, at least 2.8, at least 2.9, or at least 3.0. In some embodiments, the ratio of hydrogen to carbon monoxide in the final synthesis gas may be at least 2.25. In further embodiments, the ratio of hydrogen to carbon monoxide in the final synthesis gas may be no greater than 5.0, no greater than 4.9, no greater than 4.8, no greater than 4.7, no greater than 4.6, no greater than 4.5, no greater than 4.4, no greater than 4.3, no greater than 4.2, no greater than 4.1, no greater than 4.0, no greater than 3.9, no greater than 3.8, no greater than 3.7, no greater than 3.6, no greater than 3.5, no greater than 3.4, no greater than 3.3, no greater than 3.2, no greater than 3.1, no greater than 3.0, no greater than 2.9, no greater than 2.8, no greater than 2.7, no greater than 2.6, no greater than 2.5, no greater than 2.4, no greater than 2.3, no greater than 2.2, or no greater than 2.1. As such, the ratio of hydrogen to carbon monoxide in the final synthesis gas may be in the range of 1.5 to 5.0, 2.0 to 5.0, 2.0 to 4.0, or 2.0 to 3.0.

The following sections provide the approach followed from which a non-limiting example of method for processing methane according to the present disclosure can be made. Although specific approaches are given in the sections below, the approaches provided herein do not encompass all possible options. Rather, the present inventors determined that the approaches given in the sections below represent possible approaches that can produce suitable embodiments of a method for processing methane. Persons having ordinary skill in the art will appreciate that variations of the following examples are possible within the scope of the invention, which is defined solely by the claims. A detailed discussion on the processes and embodiments is given at the end of this section.

Figure 1:
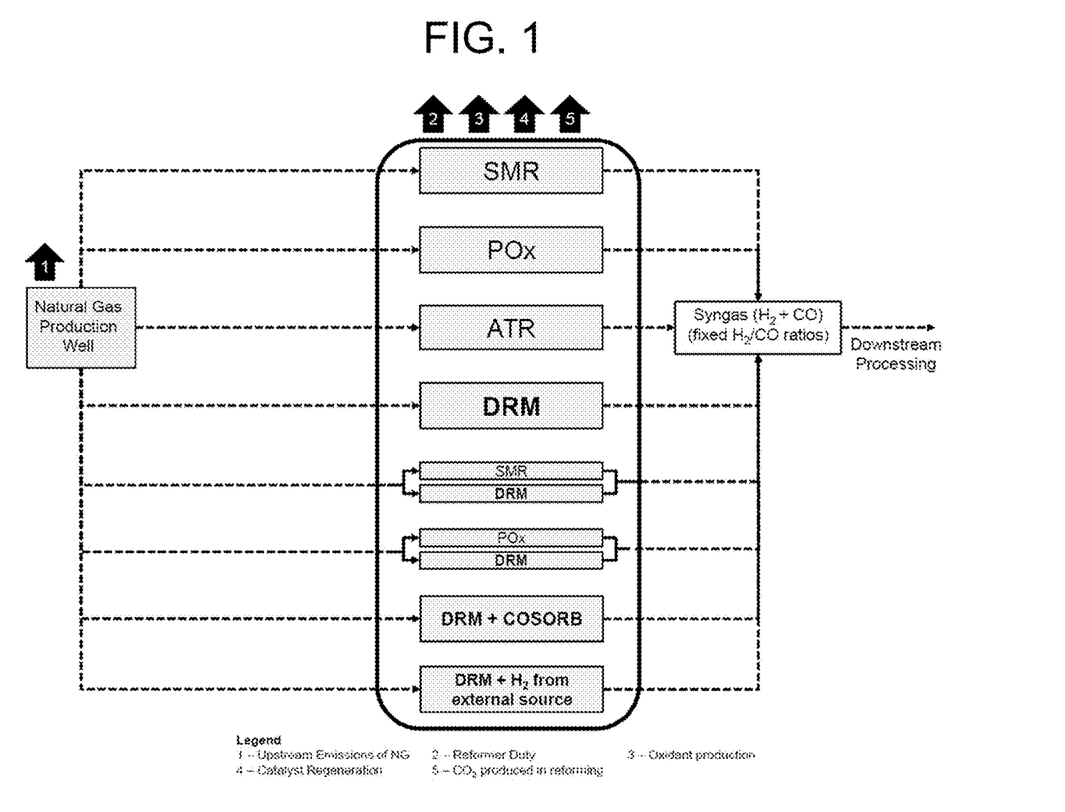
FIG. 1 is a schematic diagram showing major sources of CO₂ emissions considered for comparison.

Major sources of emissions in syngas production pathways were quantified and the performance of each case is measured in terms of overall $CO_2$ emissions and operating costs. An optimization-based approach was used to find operating points which maximize syngas production, and the carbon footprint of these points was calculated. The results point towards the regions of operation and specific scenarios where DRM might have commercial as well as environmental advantage over conventional processes. FIG. 1 shows the non-limiting examples of all the major sources of $CO_2$ emissions involved in syngas production processes which have been considered in the optimization study.

Oxidant is the source of oxygen for the production of syngas in reforming. The production of oxidant in each reformer comes with its own greenhouse gas emissions due to energy use and other factors. The $CO_2$ emissions involved in the production of these oxidants are listed in Table 1.

TABLE 1

Carbon footprint for oxidant production

| Oxidant | Carbon footprint ($CO_2$ basis) | Notes/Reference |
|---|---|---|
| Steam | 470.8 g/kg steam | GREET ® Model |
| Oxygen | 272.9 g/kg $O_2$ | GREET ® Model |
| $CO_2$ | 62.95 g/kg $CO_2$ | David and Herzog, The cost of carbon capture, Energy 2000, 13-16. |

The GREET® Model considers the energy in the generation of steam and production of pure oxygen from air and reports the associated emissions on the $CO_{2e}$ basis. The carbon footprint for $CO_2$ reported in the literature is based on $CO_2$ capture from flue gas (assuming 3% concentration in flue gas based on Natural-gas fired power plant flue gas and capture efficiency of 90%). This is a conservative estimate of the Global Warming Potential associated with using $CO_2$ for DRM. If a concentrated $CO_2$ source is available (for example, $CO_2$ as a byproduct in the production of ammonia or from midstream acid gas removal section in LNG plants) that can be directly fed to the DRM reactor, this term can be excluded from the calculations.

The relative cost of syngas production by different processes has been calculated based on the feedstock costs as shown in Table 2:

TABLE 2

Feedstock Costs

| Raw Material/ Utility | Unit Cost | Notes/Reference |
|---|---|---|
| Methane | $2.8/MMBtu | US Energy Information Administration (EIA) Data for October, 2017 |
| Steam (20 bar) | $7/tonne | TLV Steam Unit Cost Calculator |
| Oxygen | $35/tonne | Vora et al. (DOE/NETL Advanced Carbon dioxide Capture R&D Program: Technology Update; 2013) |

Assuming that the $CO_2$ source needs no further treatment, $CO_2$ is assumed to be available without any cost. Examples of such streams are the $CO_2$ streams in the natural gas processing plants were the captured $CO_2$, which is of high quality is usually released into the atmosphere. The operating cost for each reformer case is based on the feedstock costs of natural gas and oxidants, fuel costs for the furnace duties and cost savings due to heat integration. In the special case of DRM+COSORB, the cost of COSORB unit operation and the profit from selling CO to an external customer was also considered (where applicable). It should be highlighted here that cost comparisons of different technologies should be only done at same syngas ratios.

The reformer model works on the principle of minimizing the Gibbs free energy of the involved species while accounting for temperature and pressure dependence as well as the possibility of coke formation. Reformer pressure was set at 20 bar in each case. The reformer model was the main part of the overall optimization model. The results from the optimization model are discussed herein. The environmental metric to compare different reforming processes was the overall carbon footprint (kg $CO_2$/kg syngas produced) for specific syngas ratios and the operating cost was compared based on $/kmol of syngas.

Conventional Reforming Technologies

For SMR, the steam-to-carbon ratio is set to a minimum of 2 and at this ratio and between an operating temperature of 850° C. and 950° C., syngas produced has a $H_2$/CO ratio of about 3.75. Any additional steam introduced will result in syngas with higher $H_2$/CO ratios. Typical industrial steam reformers operate at these high steam-to-carbon ratios primarily to prevent coke formation and also in some cases to maintain a higher partial pressure of $H_2$ in downstream synthesis. E.g., some methanol plants operate at a higher than required $H_2$ in the methanol synthesis loop. SMR is the only available technology to produce high $H_2$/CO ratio syngas. Oxygen or $CO_2$ do not help to meet the stoichiometric requirements and hence SMR is the only option. As evident from FIG. 2, SMR has a significantly high carbon footprint due to the excess steam required based on the S/C constraint set for SMR.

In Partial Oxidation, where pure oxygen is the only oxidant used, based on equilibrium calculations, the syngas produced has a $H_2$/CO ratio of about 1.8. Since a constraint of S/C ratio of 0.1 was added as per industrial conditions, the syngas produced here has a slightly higher syngas ratio closer to 2.

In Auto-thermal Reformer (ATR), an S/C of 0.6 to 0.9 is allowed and hence ATR is able to produce syngas of higher $H_2$/CO ratios than POx. Due to the subsequent addition of steam at increasing syngas ratio which moves it from slightly exothermic range (POx) to a highly endothermic region (SMR), we see a sharp increase in the overall carbon footprint due to increasing furnace duties.

Figure 3:
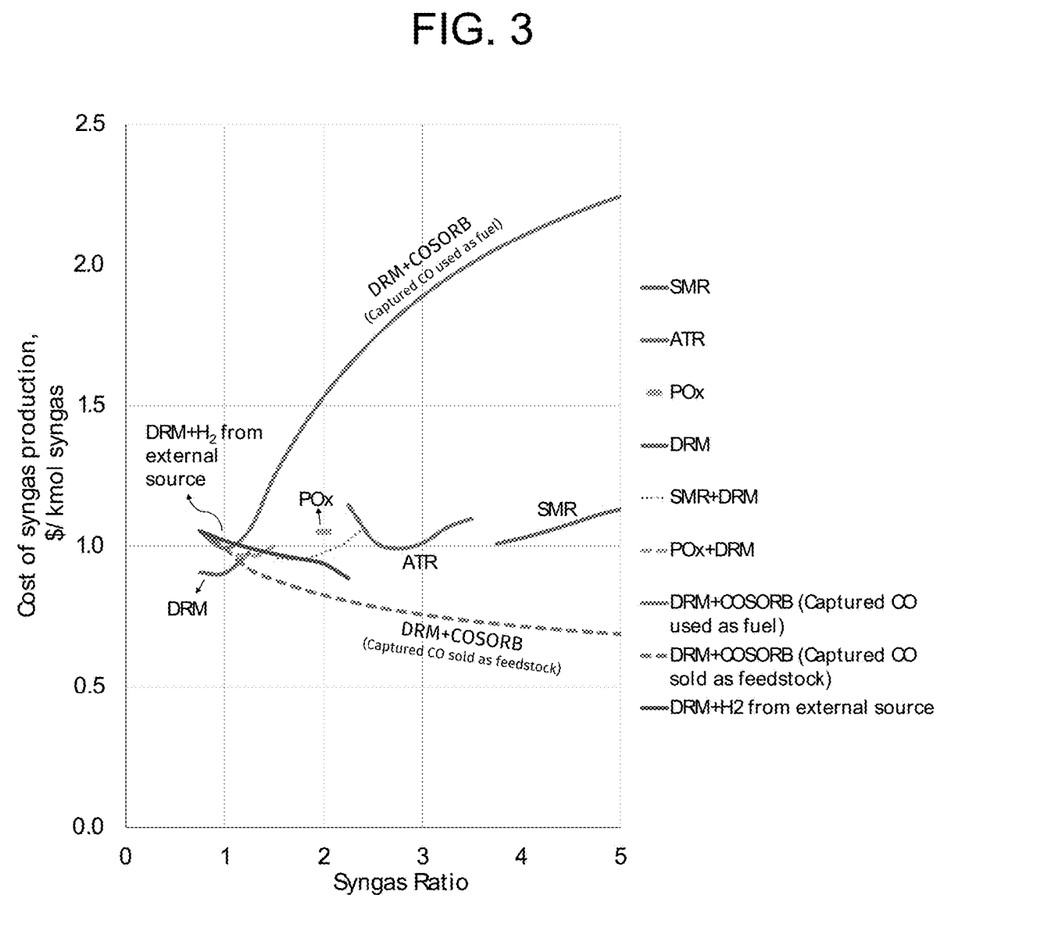
FIG. 3 is a graph plotting cost of syngas production by various processes.

These results were the benchmark and new reforming options according to the present disclosure were compared to these carbon footprints at different syngas ratios to quantify the benefit. The operating costs of SMR, ATR and POx at different syngas ratios are shown in FIG. 3. The operating cost for SMR shows an increase due to increased use of steam and reformer duties to produce higher syngas ratios. The ATR has an option between oxygen and steam. As syngas ratio increases beyond 2.25, oxygen contribution decreases and steam contribution increases. The ATR operating cost shows a decreasing trend due to oxidant cost (steam is cheaper than oxygen) and the increasing trend is due to increasing energy costs (moving from exothermic POx to endothermic SMR).

Dry Reforming of Methane

Figure 2:
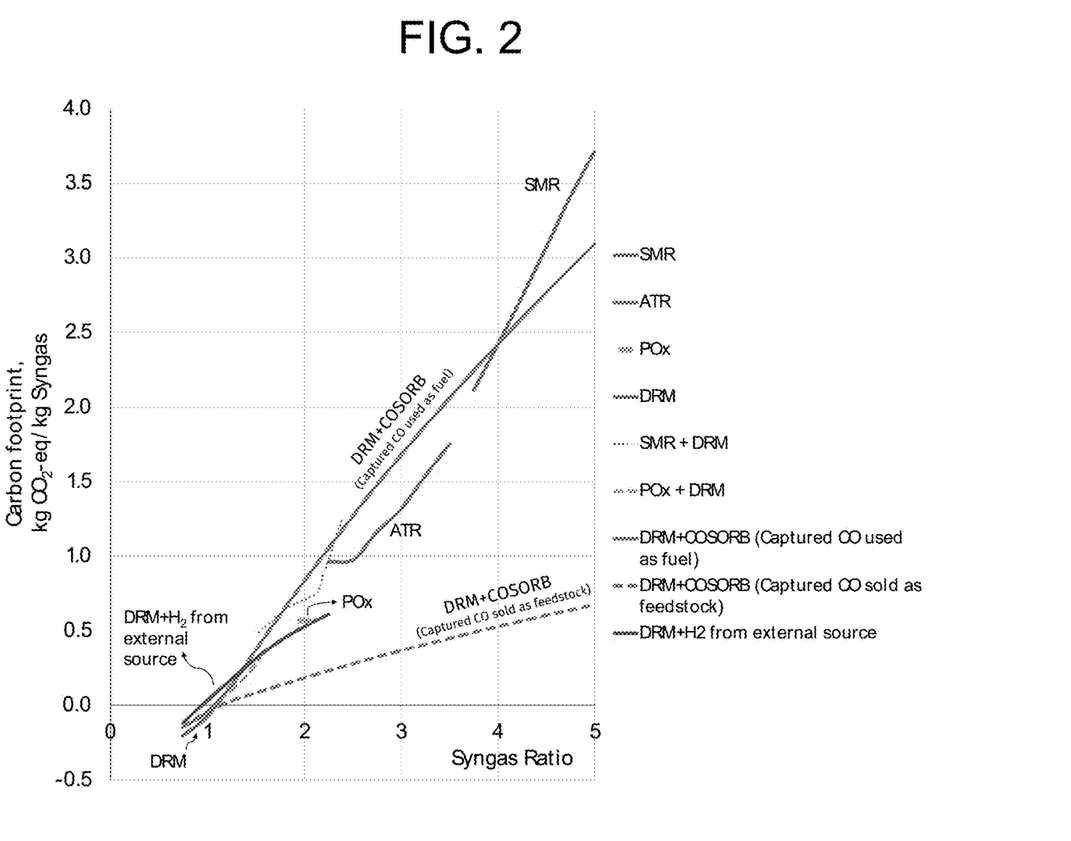
FIG. 2 is a graph plotting carbon footprint of syngas production for various processes.

A DRM unit operating as stand-alone unit will only be able to produce low syngas ratios due to stoichiometric limitations. FIG. 2 shows the carbon footprint of syngas produced by DRM for syngas ratio from 0.75 to 1.25. Syngas with $H_2$/CO ratio of 1.25 is made possible due to some steam used to maintain the S/C ratio of 0.1 and when some methane is converted to coke releasing the hydrogen. This coke is later removed by burning during the catalyst regeneration process. As indicated in FIG. 2, it is possible for DRM to operate in the negative region of the y-axis, (indicating that the DRM unit acts as a net $CO_2$ sink) albeit at low syngas ratios (1 and less than 1).

Though the Optimization model is able to select temperatures between 700° C. to 1100° C., it invariably selects the highest temperature (1100° C.) to maximize the syngas production, based on the objective function. Since the DRM is limited by the syngas ratio it can operate in, parallel combinations of SMR+DRM and POx+DRM can be made to make-up the syngas. An equally sized DRM unit is operated in parallel to existing SMR and POx unit. As is clear from the comparison of carbon footprints in FIG. 2, the parallel combination has no perceivable benefit in terms of reduction of overall $CO_2$ emissions. However, in some operating region of syngas ratios, there is a very small economic benefit in using the parallel combination. The comparison, in terms of carbon footprint and operating cost, of all benchmark syngas production technologies with the proposed designs in this invention are shown in FIG. 2 and FIG. 3.

DRM+COSORB Process (and Additional Embodiments)

As evident from the results of $CO_2$ emissions comparison in FIG. 2, though DRM was able to achieve a near zero carbon footprint, this happened only at low syngas ratios of around 1 which are not so attractive economically. To work around the bottleneck of syngas ratio, CO removal from syngas produced by DRM was studied as an option to boost $H_2$:CO ratio of DRM syngas. To employ this, an industrially tested process called COSORB has been used. COSORB is a typical absorption/desorption process with a toluene based solvent containing $CuAlCl_4$. This process has many benefits over other separation processes such as cryogenic separation or copper liquor process.

Figure 4:
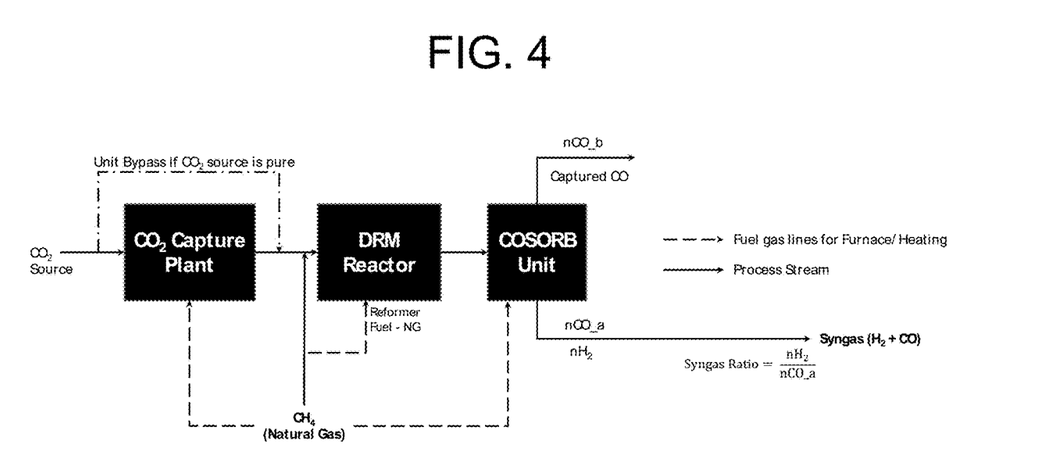
FIG. 4 is a schematic diagram showing a DRM+COSORB process according to an embodiment of the present disclosure.

Referring to FIG. 4, a schematic overview of a method in accordance with an embodiment of the present disclosure is shown, wherein the DRM syngas is sent to the COSORB unit to capture CO. Since the product syngas still needs some CO, the COSORB unit can be operated below its maximum separation efficiency thereby reducing energy consumption and allowing just enough CO (nCO_a) to remain in the syngas stream.

Figure 5:
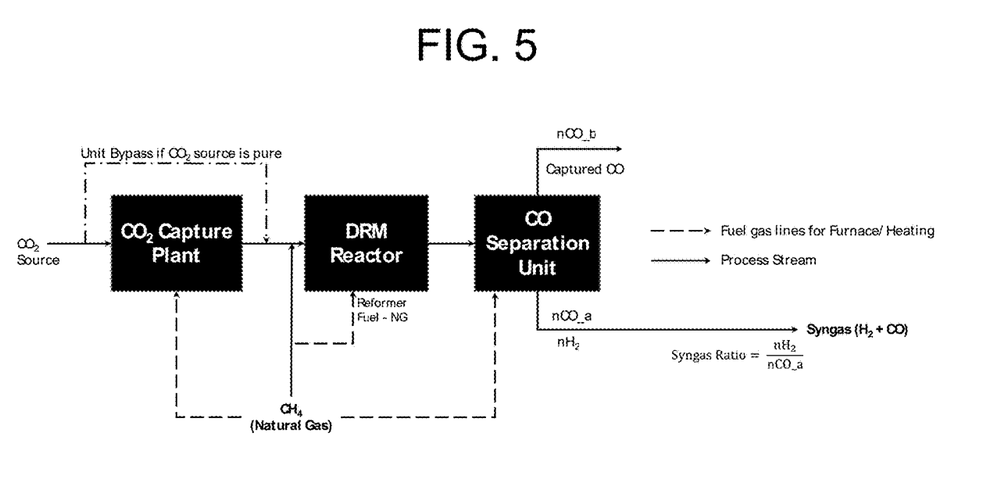
FIG. 5 is a schematic diagram showing another non-limiting embodiment of a method of the present disclosure for dry reforming of methane.
Figure 6:
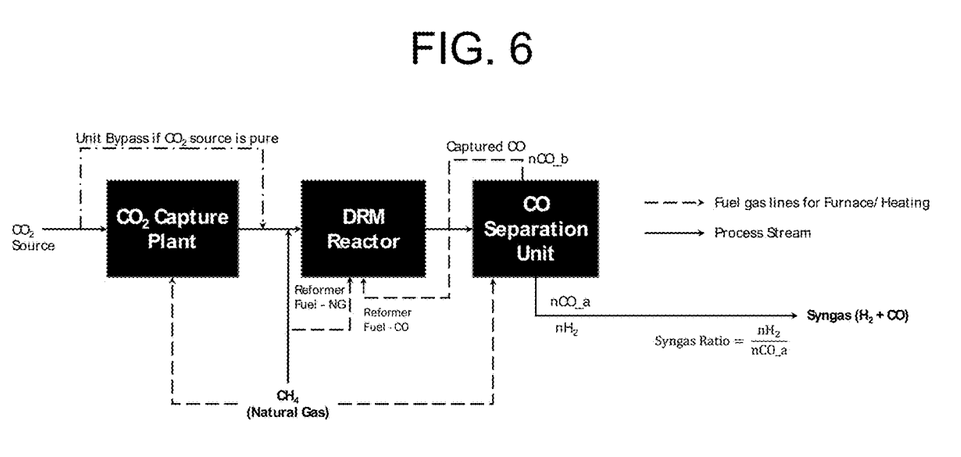
FIG. 6 is a schematic diagram showing another non-limiting embodiment of a method of the present disclosure for dry reforming of methane, where the captured CO is used as a fuel in the reformer furnace.

One embodiment of this process is shown in FIG. 5, where the COSORB is replaced with any CO Separation process. This could be any of the available processes including cryogenic separation, membrane separation, Pressure Swing Adsorption (PSA) or Temperature Swing Adsorption (TSA). Another embodiment of this process is shown in FIG. 6, wherein the captured CO can be used as a reformer fuel internally instead of a sale to an external customer.

Figure 7:
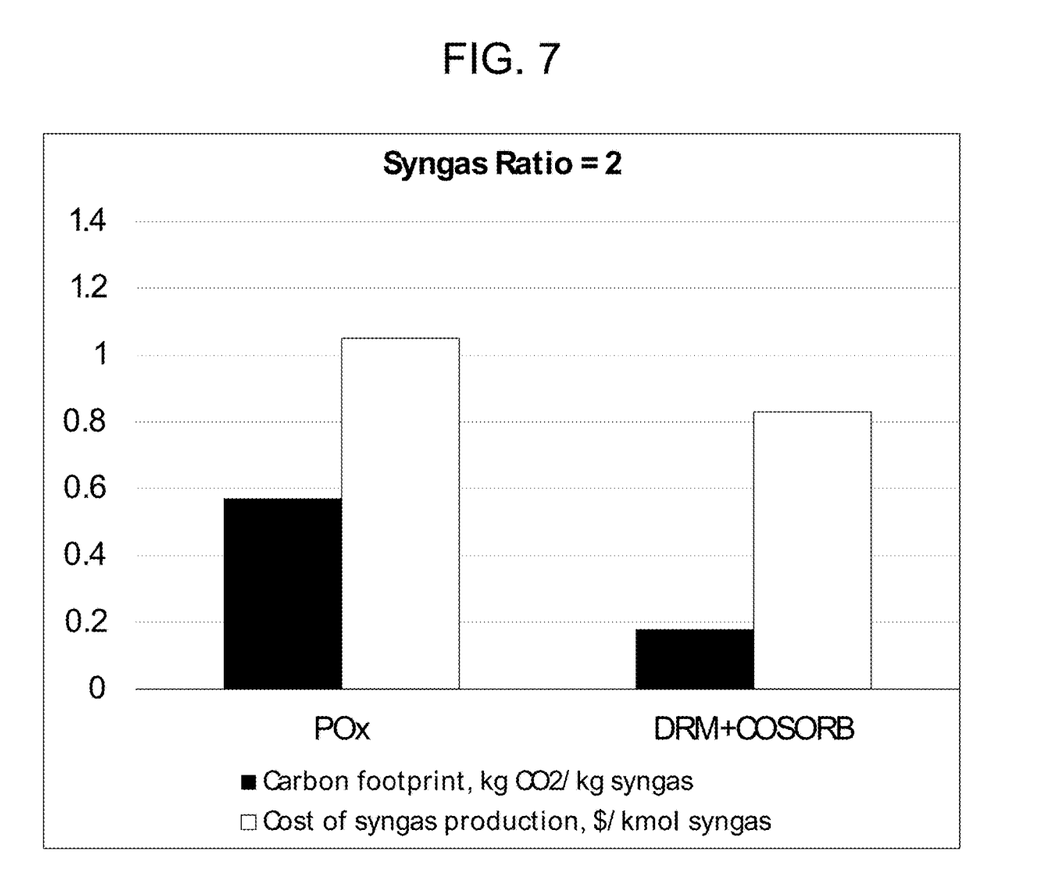
FIG. 7 shows a comparison of POx and DRM+COSORB, where captured CO is sold as feedstock, for a ratio of hydrogen to carbon monoxide in the final synthesis gas of 2.
Figure 8:
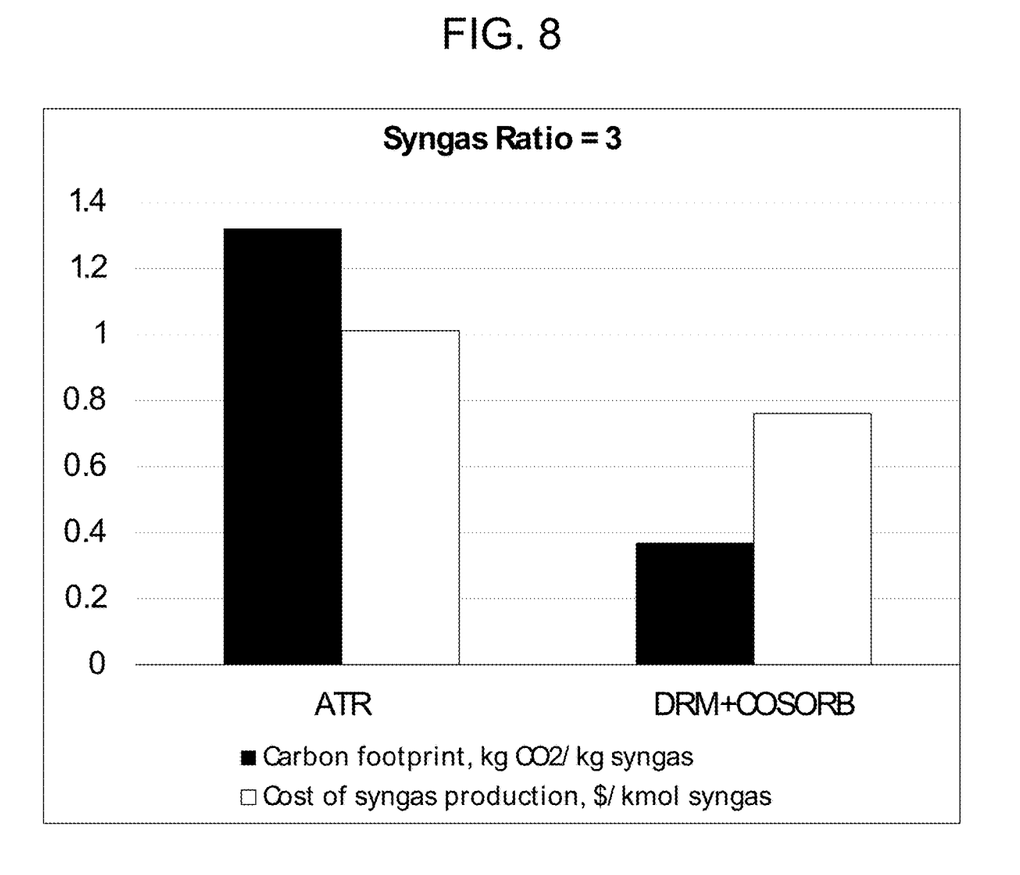
FIG. 8 shows a comparison of ATR and DRM+COSORB, where captured CO is sold as feedstock, for a ratio of hydrogen to carbon monoxide in the final synthesis gas of 3.

Each of the embodiments shown above will have implications in terms of $CO_2$ emissions and operating costs. For the cases where the captured CO is sold to an external plant (where it will utilized as a feedstock), there is a net reduction in terms of $CO_2$ emissions as well as significant cost benefit when compared to existing processes at high syngas ratios of 2 and 3. This comparison is shown in FIGS. 7-8. For a syngas ratio of 2, the DRM+COSORB unit will have more than 60% reduction in $CO_2$ emissions when compared to POx and more than 70% reduction in $CO_2$ emissions when compared to ATR for a syngas ratio of 3. For a syngas ratio of 4, the DRM+COSORB unit will likewise have a reduction in $CO_2$ emissions when compared to SMR. Assuming a sale price of $75/tonne for the captured CO, the operating cost is significantly less than that of existing processes as shown in FIG. 3. A 20% reduction in operating cost is projected for the DMR+COSORB when compared to POx for a syngas ratio of 2. When compared to ATR at a syngas ratio of 3, there is a 25% reduction in the operating cost of the DRM+COSORB unit. When compared to SMR at a syngas ratio of 4, there is a 30% reduction in the operating cost of the DRM+COSORB unit. These results are shown in Table 3.

TABLE 3

Reduction in $CO_2$ emissions and cost benefit of DRM + COSORB process, where captured CO is sold as feedstock

| Syngas Ratio | Units | POx | ATR | SMR | DRM + COSORB (Captured CO sold as feedstock) | % Change |
|---|---|---|---|---|---|---|
| 2 | kg $CO_2$/kg syngas | 0.57 | | | 0.18 | −68 |
|   | $/kmol syngas | 1.05 | | | 0.83 | −21 |
| 3 | kg $CO_2$/kg syngas | | 1.32 | | 0.37 | −72 |
|   | $/kmol syngas | | 1.01 | | 0.76 | −25 |
| 4 | kg $CO_2$/kg syngas | | | 2.43 | 0.53 | −78 |
|   | $/kmol syngas | | | 1.03 | 0.72 | −30 |

This shows that the combination of DRM+COSORB has great potential in terms of reduction in $CO_2$ emissions as well as being competitive in terms of operating costs for syngas production at high syngas ratios when the captured CO is sold to an external plant.

If the captured CO is used as a fuel as shown in FIG. 6, the overall carbon footprint can exceed conventional reformers up to a syngas ratio of 4. This can be attributed to the lower calorific value of CO which is 282.8 kJ/mol whereas for methane from natural gas, the calorific value is 890.8 J/mol. And combustion of both methane and CO yields $CO_2$ which is a penalty. The cost of operation of such a setup would be higher than conventional reformers as shown in FIG. 3, mainly due to the reduced yield of syngas/mole of natural gas since much of the CO from syngas is routed as fuel.

DRM+$H_2$ from Ethylene Process (and Additional Embodiments)

Figure 9:
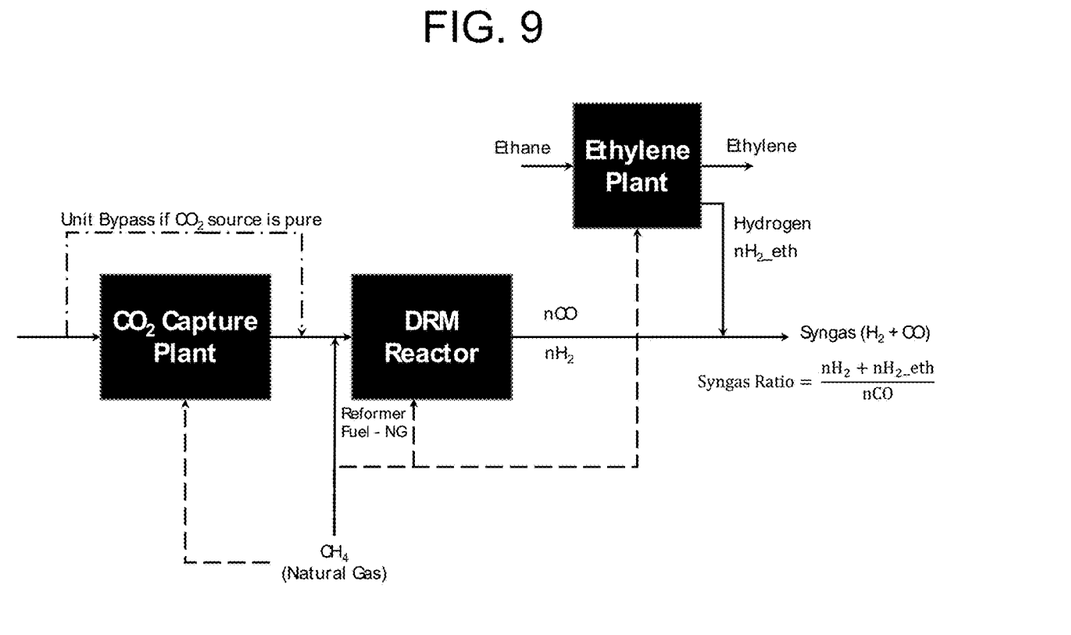
FIG. 9 is a schematic diagram showing another non-limiting embodiment of a method of the present disclosure for dry reforming of methane, where a DRM unit is integrated with an ethylene plant.
Figure 10:
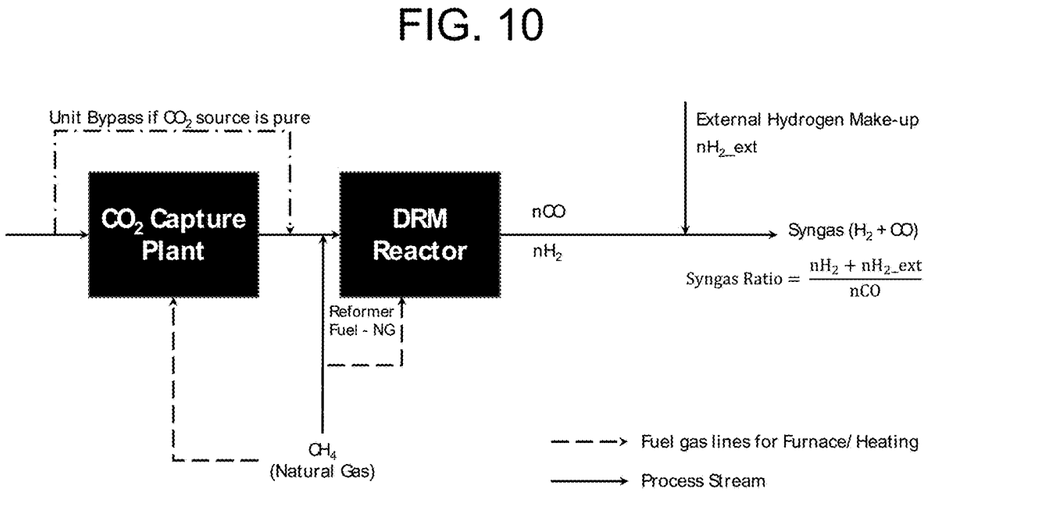
FIG. 10 is a schematic diagram showing another non-limiting embodiment of a method of the present disclosure for dry reforming of methane, where an external $H_2$ source is used.

FIG. 9 illustrates a method for dry reforming of methane according to another embodiment of the invention. This embodiment supplements the DRM syngas with external hydrogen available from an ethylene plant. Another embodiment is shown in FIG. 10 where instead of the ethylene, the external hydrogen can be supplied from any external source. In a typical ethylene plant, the hydrogen obtained after dehydrogenation of ethane is usually used as fuel in the furnaces. Though it is not a preferred fuel due to its low heating value, a typical ethylene plant does not usually have a hydrogen sink like a hydrocracker in an oil refinery. This presents an opportunity for mass integration with a DRM unit wherein the hydrogen can be blended with DRM to produce syngas of higher $H_2$:CO ratio and the hydrogen fuel can be substituted by methane in natural gas. In some embodiments, the amount of hydrogen may limit the plant size of the syngas production unit.

The hydrogen fuel on combustion does not yield $CO_2$ and hence the $CO_2$ generated due to methane combustion has to be included in the carbon footprint of the syngas production unit. Additionally, the upstream emissions for the natural gas fuel should also be included. The amount of methane needed can be calculated by equating the energy duty that was initially supplied by hydrogen (Calorific Value of Hydrogen is 284 kJ/mol).

The carbon footprint results and operating costs comparison are shown in FIG. 2 and FIG. 3 respectively. The results indicate reductions in both the $CO_2$ emissions and operating costs. For a syngas ratio of 2, there is a slight reduction of 7% in the overall $CO_2$ emissions and 11% reduction in operating costs over a POx unit. This shows that in cases where a sufficiently large hydrogen stream is available, substituting the hydrogen fuel with natural gas and using the hydrogen to boost syngas ratio of DRM syngas might be a slightly better option economically.

Various non-exhaustive, non-limiting aspects of methods for processing methane according to the present disclosure may be useful alone or in combination with one or more other aspect described herein. Without limiting the foregoing description, in a first non-limiting aspect of the present disclosure, the comprises: processing methane in presence of a carbon dioxide stream, whereby a synthesis gas including carbon monoxide and hydrogen is produced; and contacting the synthesis gas with a carbon monoxide-absorbing solution, thereby removing at least a portion of the carbon monoxide and producing a final synthesis gas having an increased ratio of hydrogen to carbon monoxide.

In accordance with a second non-limiting aspect of the present disclosure, which may be used in combination with the first aspect, processing the methane can include dry reforming of methane.

In accordance with a third non-limiting aspect of the present disclosure, which may be used in combination with each or any of the above-mentioned aspects, the removed carbon monoxide can be used as a fuel.

In accordance with a fourth non-limiting aspect of the present disclosure, which may be used in combination with each or any of the above-mentioned aspects, the removed carbon monoxide can be used as feedstock for an external plant.

In accordance with a fifth non-limiting aspect of the present disclosure, which may be used in combination with each or any of the above-mentioned aspects, the carbon dioxide stream can be provided in a form of concentrated carbon dioxide.

In accordance with a sixth non-limiting aspect of the present disclosure, which may be used in combination with each or any of the above-mentioned aspects, the ratio of hydrogen to carbon monoxide in the final synthesis gas can be at least 1.5.

In accordance with a seventh non-limiting aspect of the present disclosure, which may be used in combination with each or any of the above-mentioned aspects, the ratio of hydrogen to carbon monoxide in the final synthesis gas can be at least no greater than 3.0.

In accordance with an eighth non-limiting aspect of the present disclosure, which may be used in combination with each or any of the above-mentioned aspects, the ratio of hydrogen to carbon monoxide in the final synthesis gas can be in the range of 2.0 to 5.0.

In accordance with a ninth non-limiting aspect of the present disclosure, a method for processing methane comprises: processing methane in presence of a carbon dioxide stream, whereby a synthesis gas including carbon monoxide and hydrogen is produced; and blending the synthesis gas with hydrogen provided from an ethylene plant, thereby producing a final synthesis gas having an increased ratio of hydrogen to carbon monoxide.

In accordance with a tenth non-limiting aspect of the present disclosure, which may be used in combination with each or any of the above-mentioned aspects, processing the methane can include dry reforming of methane.

In accordance with a eleventh non-limiting aspect of the present disclosure, which may be used in combination with each or any of the above-mentioned aspects, the carbon dioxide stream can be provided in a form of concentrated carbon dioxide.

In accordance with a twelfth non-limiting aspect of the present disclosure, which may be used in combination with each or any of the above-mentioned aspects, the ratio of hydrogen to carbon monoxide in the final synthesis gas can be at least 1.5.

In accordance with a thirteenth non-limiting aspect of the present disclosure, which may be used in combination with each or any of the above-mentioned aspects, the ratio of hydrogen to carbon monoxide in the final synthesis gas can be at least 2.0.

In accordance with a fourteenth non-limiting aspect of the present disclosure, which may be used in combination with each or any of the above-mentioned aspects, the ratio of hydrogen to carbon monoxide in the final synthesis gas can be in the range of 2.0 to 5.0.

In accordance with a fifteenth non-limiting aspect of the present disclosure, a method for processing methane comprises: processing methane in presence of a carbon dioxide stream, whereby a synthesis gas including carbon monoxide and hydrogen is produced; and blending the synthesis gas with hydrogen provided from an external source, thereby producing a final synthesis gas having an increased ratio of hydrogen to carbon monoxide.

In accordance with a sixteenth non-limiting aspect of the present disclosure, which may be used in combination with each or any of the above-mentioned aspects, processing the methane can include dry reforming of methane.

In accordance with a seventeenth non-limiting aspect of the present disclosure, which may be used in combination with each or any of the above-mentioned aspects, the carbon dioxide stream can be provided in a form of concentrated carbon dioxide.

In accordance with a eighteenth non-limiting aspect of the present disclosure, which may be used in combination with each or any of the above-mentioned aspects, the ratio of hydrogen to carbon monoxide in the final synthesis gas can be at least 1.5.

In accordance with a nineteenth non-limiting aspect of the present disclosure, which may be used in combination with each or any of the above-mentioned aspects, the ratio of hydrogen to carbon monoxide in the final synthesis gas can be at least 2.0.

In accordance with a twentieth non-limiting aspect of the present disclosure, which may be used in combination with each or any of the above-mentioned aspects, the ratio of hydrogen to carbon monoxide in the final synthesis gas can be in the range of 2.0 to 5.0.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method for processing methane, the method comprising:
    processing methane in presence of a carbon dioxide stream, whereby a synthesis gas including carbon monoxide and hydrogen is produced; and
    contacting the synthesis gas with a carbon monoxide-absorbing solution, thereby removing at least a portion of the carbon monoxide and producing a final synthesis gas having an increased ratio of hydrogen to carbon monoxide,
    wherein the ratio of hydrogen to carbon monoxide in the final synthesis gas is in the range of 1.5 to 5.0.

2. The method of claim 1, wherein processing the methane includes dry reforming of methane.

3. The method of claim 1, wherein the removed carbon monoxide is used as a fuel.

4. The method of claim 1, wherein the removed carbon monoxide is used as feedstock for an external plant.

5. The method of claim 1, wherein the ratio of hydrogen to carbon monoxide in the final synthesis gas is in the range of 1.5 to 3.0.

6. The method of claim 1, wherein the ratio of hydrogen to carbon monoxide in the final synthesis gas is in the range of 2.0 to 5.0.

* * * * *